United States Patent
Prencipe

(10) Patent No.: US 9,005,586 B2
(45) Date of Patent: *Apr. 14, 2015

(54) DENTIFRICE CONTAINING ZINC IONS AND POLYPHOSPHATE IONS

(71) Applicant: Colgate-Palmolive Company, New York, NY (US)

(72) Inventor: Michael Prencipe, Princeton Junction, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/098,635

(22) Filed: Dec. 6, 2013

(65) Prior Publication Data

US 2014/0099347 A1    Apr. 10, 2014

Related U.S. Application Data

(63) Continuation of application No. 11/668,821, filed on Jan. 30, 2007, now Pat. No. 8,628,755.

(51) Int. Cl.
| | | |
|---|---|---|
| *A61K 8/00* | (2006.01) | |
| *A61K 8/33* | (2006.01) | |
| *A61K 8/24* | (2006.01) | |
| *A61K 8/25* | (2006.01) | |
| *A61K 8/27* | (2006.01) | |
| *A61Q 11/00* | (2006.01) | |
| *A61K 8/21* | (2006.01) | |
| *A61K 8/41* | (2006.01) | |
| *A61K 8/42* | (2006.01) | |
| *A61K 8/43* | (2006.01) | |
| *A61K 8/49* | (2006.01) | |
| *A61K 8/55* | (2006.01) | |
| *A61K 8/58* | (2006.01) | |
| *A61K 8/64* | (2006.01) | |

(52) U.S. Cl.
CPC ... *A61K 8/33* (2013.01); *A61K 8/24* (2013.01); *A61K 8/25* (2013.01); *A61K 8/27* (2013.01); *A61Q 11/00* (2013.01); *A61K 8/21* (2013.01); *A61K 8/416* (2013.01); *A61K 8/42* (2013.01); *A61K 8/43* (2013.01); *A61K 8/49* (2013.01); *A61K 8/4926* (2013.01); *A61K 8/4953* (2013.01); *A61K 8/4973* (2013.01); *A61K 8/55* (2013.01); *A61K 8/58* (2013.01); *A61K 8/64* (2013.01); *A61K 2800/412* (2013.01)

(58) Field of Classification Search
None
See application file for complete search history.

(56) References Cited

U.S. PATENT DOCUMENTS

| | | |
|---|---|---|
| 4,022,880 A | 5/1977 | Vinson et al. |
| 4,100,269 A | 7/1978 | Pader |
| 4,138,477 A | 2/1979 | Gaffar |
| 4,340,583 A | 7/1982 | Wason |
| 4,416,867 A | 11/1983 | Ritchey et al. |
| 4,420,312 A | 12/1983 | Wason |
| 4,421,527 A | 12/1983 | Wason |
| 4,425,325 A | 1/1984 | Ritchey et al. |
| 4,568,540 A | 2/1986 | Asano et al. |
| 4,627,977 A | 12/1986 | Gaffar et al. |
| 5,000,944 A * | 3/1991 | Prencipe et al. ............ 424/57 |
| 5,354,551 A | 10/1994 | Schmidt |
| 5,651,958 A | 7/1997 | Rice |
| 5,658,553 A | 8/1997 | Rice |
| 5,716,600 A | 2/1998 | Zahradnik et al. |
| 5,939,051 A | 8/1999 | Santalucia et al. |
| 6,290,933 B1 | 9/2001 | Durga et al. |
| 6,696,045 B2 | 2/2004 | Yue et al. |
| 2003/0124067 A1 | 7/2003 | Yue et al. |

FOREIGN PATENT DOCUMENTS

WO    WO 02/45678    6/2002

OTHER PUBLICATIONS

Brunauer et al. "Adsorption of Gases in Multimolecular Layers". Journal of the American Chemical Society. 60, 309-319. (1938).
John J. Hefferren. "A Laboratory Method for Assessment of Dentifrice Abrasivity". Journal of Dental Research. 55:4, 563-573. (1976).

* cited by examiner

*Primary Examiner* — Snigdha Maewall
(74) *Attorney, Agent, or Firm* — Howard C. Lee

(57) ABSTRACT

The invention includes a dentifrice composition that comprises a zinc ion source, a polyphosphate ion source, an anethole and a silica. The silica has a mean particle size of about 5 to about 12 microns, an Einlehner hardness of about 1 to about 20, and an oil absorption of about 40 to less than about 100 cc/100 g. The composition contains zinc ions and polyphosphate ions in a weight ratio of about 0.1:1 to about 10:1 and has a RDA value of about 100 to about 200 and a PCR value of about 75 to about 110. Related methods are also included.

21 Claims, No Drawings

DENTIFRICE CONTAINING ZINC IONS AND POLYPHOSPHATE IONS

CROSS-REFERENCE TO RELATED APPLICATIONS

This application is a continuation of U.S. application Ser. No. 11/668,821, filed Jan. 30, 2007, now U.S. Pat. No. 8,628,755, the contents of which are hereby incorporated by reference in its entirety.

BACKGROUND OF THE INVENTION

The antibacterial effects of zinc ions in the oral cavity are described in the art and numerous attempts have been made to prepare dentifrice compositions incorporating zinc ions to take advantage of the therapeutic benefits of reduced plaque, gum inflammation and/or gingivitis. However, such formulations are noted for their unpleasant taste, often referred to as "astringent". Such unpleasant organoleptic experiences often result in reduced compliance to an oral care regimen by the patient/consumer.

Various attempts to disguise or avoid the unpleasant organoleptic aspects while retaining and/or enhancing the therapeutic benefits obtained have been made. However, there remains a need in the art for a dentifrice formulation that allows the patient/consumer to obtain the therapeutic benefits of a zinc-containing dentifrice, whilst not suffering the disadvantageous organoleptic experience associated with such dentifrices.

BRIEF SUMMARY OF THE INVENTION

The invention includes a dentifrice composition that comprises a zinc ion source, a polyphosphate ion source, an anethole, and a silica. The silica has a mean particle size of about 5 to about 12 microns, an Einlehner hardness of about 1 to about 20, and an oil absorption of about 40 to less than about 100 cc/100 g. The composition contains zinc ions and polyphosphate ions in a weight ratio of about 0.1:1 to about 10:1 and has a RDA value of about 100 to about 200 and a PCR value of about 75 to about 110. In one embodiment, the zinc ion source is zinc citrate.

The invention also includes related methods, such as a method of maintaining and/or enhancing systemic health that includes topically applying the dentifrice composition of the invention at least once a day to an oral surface, or a method of reducing the presence of plaque on an oral surface comprising topically applying an oral care composition at least once a day to an oral surface.

DETAILED DESCRIPTION OF THE INVENTION

The invention described herein provides clinical efficacy in an oral context, yet is not perceived by the patient as having the unpleasant astringent taste commonly associated with conventional zinc-containing dentifrices. In one aspect, the invention includes a composition having a zinc ion source, a polyphosphate ion source, an anethole, and a silica.

Zinc ion sources for use in the invention may include agents known or to be developed in the art that ionize at least partially once applied to the oral surfaces in the presence of saliva. For example, suitable zinc ion sources may include zinc salts, such as zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880, the contents of which are incorporated herein by reference. Mixtures on two or more of these zinc ion sources may also be used. Other zinc ion sources include those described in U.S. Pat. No. 5,000,944, the contents of which are incorporated herein by reference.

The zinc ion source may be present in any effective amount; however, it may be preferable that it is present in a sufficient amount to provide at least about 1,000 ppm of zinc ions for delivery to the tooth surface or alternatively, about 2,000 ppm to about 15,000 ppm. Under some circumstances, one may wish to have the zinc ion source present in an amount sufficient to provide about 3,000 ppm to about 13,000 ppm or about 4,000 ppm to about 10,000 ppm.

Depending on the ionization properties of the zinc salt selected, it may be desirable that the zinc ion is present in the composition in an amount of about 1% by weight to about 5% by weight, alternatively 3% by weight to about 10% by weight.

A polyphosphate ion source is present in the composition of the invention. The polyphosphate ion source suitable for inclusion into the composition may include any known or to be developed in the art, as long as it ionizes at least partially to provide polyphosphate ions upon application to an oral surface. Exemplary polyphosphate ions may include linear polyphosphates, cyclic polyphosphates, dialkali or tetra alkali metal pyrophosphate salts, $Na_4P_2O_7$, $K_4P_2O_7$, $Na_2K_2P_2O_7$, $Na_2H_2P_2O_7$ and $K_2H_2P_2O_7$, alkali metal hexametaphosphates, alkali metal trimetaphosphates, glassy polyphosphates and may include those having the structure:

$$XO(XPO_3)_nX$$

wherein X is a cation such as $Na^{2+}$, $Ca^{2+}$, $Mg^{2+}$, $Fe^{2+}$, $Mn^{2+}$, and $K^{2+}$, and n is about 4 to about 125 or alternatively 10 to about 75. In some embodiments, n may be 6, 13, 21 or 63. These polyphosphates may be used alone or in any combination of two or more. Other polyphosphate ion sources include those described in U.S. Pat. No. 5,000,944, the contents of which are incorporated herein by reference.

The selected polyphosphates may be present in any amount; however, it may be preferred that the polyphosphate is present in amounts of about 0.1% to about 45% by weight of the total composition, alternatively about 20% to about 30% by weight of the total composition.

The absolute amounts of polyphosphate ion sources and zinc ion sources should be calculated such that the overall composition contains zinc ions and polyphosphate ions in a weight ratio of about 0.1:1 to about 10:1, alternatively in a weight ratio of about 0.2:1 to about 5:1.

The composition includes an anethole, which may be from any source, synthetic or natural. Any isomeric form may be used (e.g., estragol). It may be provided to the composition neat or it may be included as part of an extract of fennel, basil, star anise and the like. It may be present in any amount, for example, about 0.1% to about 10% by weight or 2% to about 7% by weight.

Silica is included in the composition of the invention. The silica has a mean particle size of about 5 to about 12 microns, alternatively about 7 to 10 microns, as measured using a Malvern Particle Size Analyzer, Model Mastersizer S. This instrument, manufactured by Malvern Instruments, Inc., Southborough, Mass., United States of America, as disclosed in U.S. Pat. No. 6,290,933, the contents of which are incorporated herein by reference.

Suitable silica for use in the composition of the invention has an Einlehner hardness of about 1 to about 20, alternatively about 5 to about 15 and an oil absorption value of about 40 to less than about 100 cc/100 g. The Einlehner hardness is determined using an Einlehner At-1000 Abrader. A Fourdrinier brass wire screen is weighed and exposed to the action of a 10% aqueous silica suspension for a given number of revolutions. The hardness value is expressed as milligrams weight lost of the Fourdrinier wire screen per 100,000 revolutions. The oil absorption value is determined using ASTM rub-out method D281.

Silicas suitable for use in the composition may also have a BET surface area of about 100 to 700 m$^2$/g of silica. The BET surface area is determined by a BET nitrogen adsorption method described in Brunauer et al., Journal of the American Chemical Society, 60, 309 (1938), the contents of which are incorporated herein by reference. The BET measurement is preformed using an Accelerated Surface Area and Porosimetry Analyzer (ASAP 2400), by Micromeritics Instrument Corporation, Norcross, Ga., United States of America. The sample is outgassed under vacuum at 350° C. for a minimum of two hours before measurement.

The composition of the invention may include any conventional dentifrice vehicle component, such as water, surfactants, sweeteners, preservatives, flavorants, colorants, and/or additional active agents. Any may be included; suitable examples include stannous ion agent; triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; a copper ion agent; a fluoride ion source, an essential oil; furanones; bacteriocins; and salts thereof.

The composition may be prepared by any means know in the art, such as, for example, the methods disclosed in WIPO Publication Number WO 2002/45678, the contents of which are incorporated herein by reference.

The final composition is characterized by a radiotracer dentin abrasion value ("RDA value") of about 100 to about 200, alternatively about 125 to about 175 and a pellicle cleaning ratio ("PCR value") about 75 to about 110, alternatively about 85 to about 97. The RDA value is determined according to the method recommended by the American Dental Association as set forth by Hefferren, Journal of Dental Research, 55:4, 1976, 563-573, and described U.S. Pat. Nos. 4,340,583; 4,420,312; and 4,421,527, the contents of each of which are incorporated herein by reference. In summary, an irradiated dentin surface is treated with the slurried composition to be evaluated and the level of radioactivity present in the slurry post treatment is indicative of the level of wear to the dentin surface.

PCR values are determined as measured by the method described U.S. Pat. Nos. 5,658,553 and 5,651,958, the contents of which are incorporated herein by reference. In summary, a clear pellicle material is applied to a bovine tooth which is then stained with a combination of the pellicle material and tea, coffee, and FeCl$_3$, which is subsequently treated with the composition, and the change in the reflectance of the tooth surface before and after treatment is the PCR value.

The invention also includes methods of maintaining and/or enhancing systemic health, reducing and/or preventing gingival inflammation, and reducing the presence of plaque on an oral surface. Such methods include topically application of any of the compositions described herein to the surfaces of the oral cavity ("oral surfaces"), such as the teeth, gingival tissue, buccal tissue, tongue surface, cheek surface, etc. Application may be accomplished by any means; such means may vary depending on the form of the primary oral care composition. Exemplary means of application include application using an implement (such as a brush, toothbrush, stick, sponge, cotton swab), lavage ("swish"), mastication, adjacent placement, and dissolution. Application can be at least once, at least twice, or more per day.

I claim:

1. A dentifrice composition comprising:
   a. a zinc ion source;
   b. a polyphosphate ion source;
   c. an anethole; and
   d. a silica, the silica having a mean particle size of about 5 to about 12 microns, an Einlehner hardness of about 1 to about 20, and an oil absorption of about 40 to less than about 100 cc/100 g,
   wherein the composition contains zinc ions and polyphosphate ions in a weight ratio of about 0.1:1 to about 10:1 and has a RDA value of about 100 to about 200 and a PCR value of about 75 to about 110;
   further comprising a methyl vinyl ether/maleic anhydride copolymer.

2. The composition of claim 1, wherein the zinc ion source is zinc citrate.

3. The composition of claim 1, wherein the zinc ion source is selected from zinc oxide, zinc sulfate, zinc chloride, zinc lactate, zinc gluconate, zinc malate, zinc tartrate, zinc carbonate and zinc phosphate.

4. The composition of claim 1, wherein the polyphosphate ion source is tetrapotassium pyrophosphate.

5. The composition of claim 1, wherein the polyphosphate ion source is selected from dialkali or tetra alkali metal pyrophosphate salts, Na$_4$P$_2$O$_7$, K$_4$P$_2$O$_7$, Na$_2$K$_2$P$_2$O$_7$, Na$_2$H$_2$P$_2$O$_7$, K$_2$H$_2$P$_2$O$_7$, and sodium hexametaphosphate, potassium trimetaphosphate.

6. The composition of claim 1, wherein the polyphosphate ion source is selected from those having the structure:

$$XO(XPO_3)_nX$$

wherein X is chosen from Na+, Ca$^{2+}$, Mg$^{2+}$, Fe$^{2+}$, Mn$^{2+}$, and K$^+$, and n is about 4 to about 125.

7. The composition of claim 1, wherein the silica has a BET surface area of about 100 to about 700 m$^2$/g of silica.

8. The composition of claim 1, wherein the zinc ions and the polyphosphate ions are present in a weight ratio of about 0.2:1 to 5:1.

9. The composition of claim 1, further comprising an agent selected from a stannous ion agent; triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; a fluoride ion source, an essential oil; furanones; and salts thereof.

10. A method of maintaining and/or enhancing systemic health comprising topically applying an oral care composition at least once a day to an oral surface, the composition comprising:
   a. a zinc ion source;
   b. a polyphosphate ion source;
   c. an anethole; and
   d. a silica, the silica having a mean particle size of about 5 to about 12 microns, an Einlehner hardness of about 1 to about 20, and an oil absorption of about 40 to less than about 100 cc/100 g,
   wherein the composition contains zinc ions and polyphosphate ions in a weight ratio of about 0.1:1 to about 10:1, and has a RDA value of about 100 to about 200 and a PCR value of about 75 to about 110; and
   further comprising a methyl vinyl ether/maleic anhydride copolymer.

11. The method of claim 10, wherein the zinc ion source is zinc citrate.

12. The method of claim 10, wherein the zinc ion source is zinc lactate.

13. The method of claim 10, wherein the zinc ion source is selected from zinc oxide, zinc sulfate, zinc chloride, zinc lactate, zinc gluconate, zinc malate, zinc tartrate, zinc carbonate, and zinc phosphate.

14. The method of claim 10, wherein the polyphosphate ion source is tetrapotassium pyrophosphate.

15. The method of claim 10, wherein the polyphosphate ion source is selected from dialkali or tetraalkali metal pyrophosphate salts, $Na_4P_2O_7$, $K_4P_2O_7$, $Na_2K_2P_2O_7$, $Na_2H_2P_2O_7$, $K_2H_2P_2O_7$, sodium hexametaphosphate, and potassium trimetaphosphate.

16. The method of claim 10, wherein the silica has a BET surface area of about 100 to about 700 $m^2/g$ of silica.

17. The method of claim 10, wherein the zinc ions and the polyphosphate ions are present in a weight ratio of 0.2:1 to about 5:1.

18. The method of claim 10, wherein the composition is topically applied to an oral surface twice a day.

19. A method of reducing the presence of plaque on an oral surface comprising topically applying an oral care composition at least once a day to an oral surface, the composition comprising:

a. a zinc ion source;
b. a polyphosphate ion source;
c. an anethole; and
d. a silica, the silica having a mean particle size of about 5 to about 12 microns, an Einlehner hardness of about 1 to about 20, and an oil absorption of about 40 to less than about 100 cc/100 g, wherein the composition contains zinc ions and polyphosphate ions in a weight ratio of about 0.1:1 to about 10:1 and has a RDA of about 100 to about 200 and a PCR value of about 75-110; and further comprising a methyl vinyl ether/maleic anhydride copolymer.

20. The method of claim 19, wherein application is accomplished by a brush, a toothbrush, a stick, a sponge, a swab, lavage, mastication and dissolution.

21. The composition of claim 3, further comprising an agent selected from a stannous ion agent; triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; a fluoride ion source, an essential oil; furanones; and salts thereof.

* * * * *